United States Patent
Hu et al.

(10) Patent No.: US 10,859,660 B2
(45) Date of Patent: Dec. 8, 2020

(54) SOFT TISSUE SIMULATOR FOR MAGNETIC RESONANCE TESTING AND METHOD FOR SIMULATED TESTING

(71) Applicant: SOOCHOW UNIVERSITY, Suzhou (CN)

(72) Inventors: Chunhong Hu, Suzhou (CN); Mo Zhu, Suzhou (CN); Xuefeng Zhao, Suzhou (CN); Long Huang, Suzhou (CN); Yuan Feng, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 408 days.

(21) Appl. No.: 15/769,333

(22) PCT Filed: Apr. 18, 2017

(86) PCT No.: PCT/CN2017/080849
§ 371 (c)(1),
(2) Date: Apr. 18, 2018

(87) PCT Pub. No.: WO2018/188105
PCT Pub. Date: Oct. 18, 2018

(65) Prior Publication Data
US 2019/0064304 A1 Feb. 28, 2019

(30) Foreign Application Priority Data

Apr. 12, 2017 (CN) .......................... 2017 1 0237378

(51) Int. Cl.
*G01R 33/58* (2006.01)
*G01R 33/20* (2006.01)
(Continued)

(52) U.S. Cl.
CPC ............... *G01R 33/58* (2013.01); *G01N 3/36* (2013.01); *G01N 33/4833* (2013.01); *G01R 33/20* (2013.01)

(58) Field of Classification Search
CPC ............. G01N 3/36; G01N 2203/0044; G01N 33/4833; G01N 2203/0005–0008;
(Continued)

(56) References Cited

U.S. PATENT DOCUMENTS 5,616,857 A * 4/1997 Merck, Jr. ................ G01N 3/42
73/82
6,078,387 A * 6/2000 Sykes ................ G01R 1/06705
356/213
(Continued)

FOREIGN PATENT DOCUMENTS

CN    104000591 A    8/2014
CN    104771170 A    7/2015
(Continued)

OTHER PUBLICATIONS

Chapter I International Preliminary Report on Patentability Translation for PCT/CN2017/080849 (Year: 2019).*
(Continued)

*Primary Examiner* — David L Singer
(74) *Attorney, Agent, or Firm* — SZDC Law P.C.

(57) ABSTRACT

A soft tissue simulator for magnetic resonance imaging and a method for simulated testing are disclosed. The simulator includes a base for supporting a soft tissue or organ sample, an indenter, a pneumatic cylinder and an air source. The pneumatic cylinder is separated into a first chamber and a second chamber. The air source includes a pneumatic generation source and a reversing valve having a first air outlet and a second air outlet which are respectively connected to the first and second chambers. The reversing valve is used to
(Continued)

control compressed air to enter the first or second chamber to control the movement of the indenter. The indenter is controlled to have a periodic or unidirectional movement, to simulate the movement of a human organ or soft tissue. The simulator can used for the measurement of physical characteristics of soft tissue based on magnetic resonance imaging.

8 Claims, 4 Drawing Sheets

(51) Int. Cl.
*G01N 3/36* (2006.01)
*G01N 33/483* (2006.01)

(58) Field of Classification Search
CPC .... G01N 2203/0019; G01N 2203/0042–0046; G01R 33/58; A61B 2017/00544–00548; A61B 5/4222–4255
See application file for complete search history.

(56) References Cited

U.S. PATENT DOCUMENTS

| | | | | |
|---|---|---|---|---|
| 6,332,364 | B1* | 12/2001 | Buschmann | G01N 3/08 73/788 |
| 8,380,281 | B2 | 2/2013 | Osman et al. | |
| 8,706,192 | B2* | 4/2014 | Li | F15B 7/00 600/421 |
| 2010/0049029 | A1* | 2/2010 | Li | A61B 5/055 600/410 |
| 2011/0006767 | A1* | 1/2011 | Sack | A61B 5/055 324/309 |
| 2011/0270079 | A1* | 11/2011 | Osman | G01R 33/56358 600/421 |
| 2013/0303882 | A1* | 11/2013 | Kolipaka | A61B 5/055 600/415 |
| 2014/0171995 | A1* | 6/2014 | McDonell | A61B 17/3203 606/170 |
| 2016/0274210 | A1* | 9/2016 | Sack | A61B 5/0051 |
| 2016/0287130 | A1* | 10/2016 | Wagshul | A61B 5/055 |
| 2017/0199108 | A1* | 7/2017 | Feng | G01N 3/08 |
| 2017/0269057 | A1* | 9/2017 | Feng | G01N 3/06 |

FOREIGN PATENT DOCUMENTS

| | | | | |
|---|---|---|---|---|
| CN | 104977211 A | * | 10/2015 | ......... G01N 33/4833 |
| CN | 105300812 A | * | 2/2016 | ............ G01N 3/066 |
| CN | 205080003 U | | 3/2016 | |
| CN | 106370519 A | | 2/2017 | |
| CN | 206638796 U | | 11/2017 | |

OTHER PUBLICATIONS

Machine Translation of CN 104771170 B (Year: 2020).*
Samani et al, Magnetic Resonance Elastography Technique for Breast Tissue In-Vitro Elasticity Measurement, Proceedings IEEE International Symposium on Biomedical Imaging (Year: 2002).*
Yu et al, Comparison of MRI-Compatible Mechatronic Systems With Hydrodynamic and Pneumatic Actuation, IEEE/ASME Transactions on Mechatronics, vol. 13, No. 3, Jun. 2008 (Year: 2008).*
Fischer et al, MRI-Compatible Pneumatic Robot for Transperineal Prostate Needle Placement, IEEE/ASME Transactions on Mechatronics, vol. 13, No. 3, Jun. 2008 (Year: 2008).*
Yu et al, fMRI-Compatible Robotic Interfaces with Fluidic Actuation, Robotics: Science and Systems IV, Eidgenössische Technische Hochschule Zürich, Zurich, Switzerland, Jun. 25-28, 2008 (Year: 2008).*
Festo, Pneumatics Basic Level (Year: 2000).*
Herzig et al, Stiffness Control of Pneumatic Actuators to Simulate Human Tissues Behavior on Medical Haptic Simulators, 2016 IEEE International Conference on Advanced Intelligent Mechatronics (AIM) Banff, Alberta, Canada, Jul. 12-15, 2016 (Year: 2016).*
Valvesonline, Valve Terminology (Year: 2017).*

* cited by examiner

SOFT TISSUE SIMULATOR FOR MAGNETIC RESONANCE TESTING AND METHOD FOR SIMULATED TESTING

This application is the national stage application of PCT/CN2017/080849, filed on Apr. 18, 2017, which claims priority to Chinese Patent Application No. CN 201710237378.7, filed on Apr. 12, 2017, which is incorporated by reference for all purposes as if fully set forth herein.

FIELD OF THE INVENTION

The present invention relates to the technical field of soft substances and experimental mechanics, and more particularly to a soft tissue simulator for magnetic resonance testing and a method for simulated testing.

DESCRIPTION OF THE RELATED ART

Testing of physical characteristics of soft tissue based on magnetic resonance is currently an important development trend of image-based clinical diagnosis. Currently, main methods for testing physical characteristics of human soft tissue based on magnetic resonance include a labeling and imaging technique, an elastography technique, and the like. A major measure is to use animal and artificial samples to perform simulated testing before new measurement methods and disease detection applications are clinically applied.

Currently, during simulated testing of a sample, a driving manner that applies displacement is mainly diaphragm driving and piezoelectric ceramic driving. When a diaphragm is used to perform driving, a driving diaphragm covers an air bladder to perform diaphragm pneumatic driving to apply displacement to the sample. The disadvantages are that it is difficult to perform simulation and testing of labeling and imaging and it is not easy to control the distribution of driving displacement. When piezoelectric ceramics are used to perform driving, displacement produced by a piezoelectric driver is transferred to an output end in a manner of a mechanical connection. The disadvantages are that it is difficult to perform simulated testing for a large sample, the amplitude of displacement has a limited adjustment range, and it is difficult to perform simulation and testing of labeling and imaging.

The main disadvantages of an existing device for performing simulated testing of a sample are:

1. The device is mainly used for a specific magnetic resonance imaging method. The driving displacement has a limited range and cannot be applied to multiple different displacement ranges of different imaging manners.

2. In a pneumatic driving manner, displacement produced in a diaphragm driving manner is not easy to control and distribution of displacement is not even.

3. Piezoelectric driving has relatively small displacement, and it is difficult to apply piezoelectric driving to the measurement of large samples.

SUMMARY OF THE INVENTION

To resolve the foregoing technical problems, the object of the present invention is to provide a soft tissue simulator for magnetic resonance testing and a method for simulated testing, so that the driving displacement has a relatively large amplitude range, samples having different sizes can be driven, displacement has even distribution, control precision is desirable, and the present invention is generally applicable to simulation of measurement of physical characteristics of soft tissue based on a magnetic resonance method.

For the above purpose, the invention utilizes the following technical solutions.

In one aspect, the invention provides a soft tissue simulator for magnetic resonance testing which includes a base for supporting a soft tissue sample, an indenter facing the sample, a pneumatic cylinder for driving the indenter to move reciprocally relative to the sample, and an air source for supplying air to the pneumatic cylinder. The pneumatic cylinder is separated into a first chamber and a second chamber by a piston, and the piston is connected to the indenter. The air source includes a pneumatic generation source and a reversing valve connected to the pneumatic generation source and having a first air outlet and a second air outlet, and the first air outlet and the second air outlet of the reversing valve are respectively connected to the first chamber and the second chamber of the pneumatic cylinder.

Preferably, an adjustment device is disposed on the base for adjusting a distance between the pneumatic cylinder and the sample, the adjustment device includes two screw rods each having an end rotatably connected to the base, a sliding platform having two ends threadedly connected to the two screw rods respectively, a top plate rotatably connected to the other end of each of the two screw rods, and a handwheel disposed on the top plate for driving the two screw rods to rotate, and the pneumatic cylinder is disposed on the sliding platform.

Preferably, the two ends of each of the screw rods are rotatably connected to the base and the top plate by a bearing respectively.

Preferably, a one-way throttle valve is connected between the pneumatic generation source and the reversing valve.

Preferably, the reversing valve is a two-position five-way solenoid reversing valve.

Preferably, the pneumatic generation source is an air compressor that produces compressed air.

In another aspect, the invention also provides a method for simulated testing using the foregoing soft tissue simulator for magnetic resonance testing, including the following steps:

(1) placing a soft tissue or organ sample having a suitable size on the base, and making the sample contact the indenter;

(2) activating the pneumatic generation source, and controlling the direction of the reversing valve, such that the first air outlet is in fluid communication with the first chamber or the second air outlet is in fluid communication with the second chamber, and the indenter retract or press the sample, and then adjusting the direction of the reversing valve, to enable the indenter to produce a periodic movement or a unidirectional movement; and (3) adjusting and controlling the pneumatic generation source based on physical and mechanical characteristics of soft tissue in magnetic resonance, to simulate the movement of a human organ or the movement of soft tissue in human testing.

In still other aspect, the invention further provides a method for simulated testing using the foregoing soft tissue simulator for magnetic resonance testing, including the following steps:

(1) placing a soft tissue or organ sample on the base, and rotating the handwheel to adjust a height of the sliding platform on the screw rods according to the size of the sample, such that the indenter contact the sample;

(2) activating the pneumatic generation source and controlling the direction of the reversing valve, such chat the first air outlet is in fluid communication with the first chamber or the second air outlet is in fluid communication with the second chamber, and the indenter retract or press the sample, and then adjusting the direction of the reversing valve, to enable the indenter to produce a periodic movement or a unidirectional movement; and (3) adjusting and controlling the pneumatic generation source based on physical and mechanical characteristics of soft tissue in magnetic resonance, to simulate the movement of a human organ or the movement of soft tissue in human testing.

In another aspect, the invention provides a method for simulated testing using the foregoing soft tissue simulator for magnetic resonance testing, including the following steps:

(1) placing a soft tissue or organ sample having a suitable size on the base and making the sample contact the indenter, or, placing a soft tissue or organ sample on the base, and rotating the handwheel to adjust a height of the sliding platform on the screw rods according to the size of the sample such that the indenter contact the sample;

(2) activating the pneumatic generation source, opening the one-way throttle valve and controlling the direction of the reversing valve, such that the first air outlet is in fluid communication with the first chamber or the second air outlet is in fluid communication with the second chamber, and the indenter retract or press the sample, and then adjusting the direction of the reversing valve, to enable the indenter to produce a periodic movement or a unidirectional movement; and (3) adjusting and controlling the pneumatic generation source based on physical and mechanical characteristics of soft tissue in magnetic resonance, to simulate the movement of a human organ or the movement of soft tissue in human testing.

By means of the foregoing solutions, the present invention has the following advantages:

1. Based on pneumatic driving, the reversing valve is used to control compressed air to evenly enter the first chamber or the second chamber of the pneumatic cylinder to control the movement of the indenter, so that displacement has even distribution and control precision is desirable.

2. The displacement of the pneumatic cylinder relative to the base can be adjusted according to the size of a sample, so that the driving displacement has a relatively large amplitude range, and the amplitude of displacement is controllable and adjustable.

3. The indenter is controlled to make a periodic movement or unidirectional movement, to simulate the movement of a human organ or the movement of soft tissue in human testing, so that the present invention is generally applicable to simulation of measurement of physical characteristics of soft tissue based on a magnetic resonance method.

The foregoing description is merely brief description of the technical solutions of the present invention. For better understanding of the technical measures of the present invention and implementation according to the content of the specification, detailed description is provided below with reference to the preferred embodiments of the present invention and the accompanying drawings.

DETAILED DESCRIPTION OF THE PREFERRED EMBODIMENTS

The invention will be further illustrated in more detail with reference to the accompanying drawings and embodiments. It should be noted that, the following embodiments only are intended for purpose of illustration, but are not intended to limit the scope of the present invention.

Figure 1:
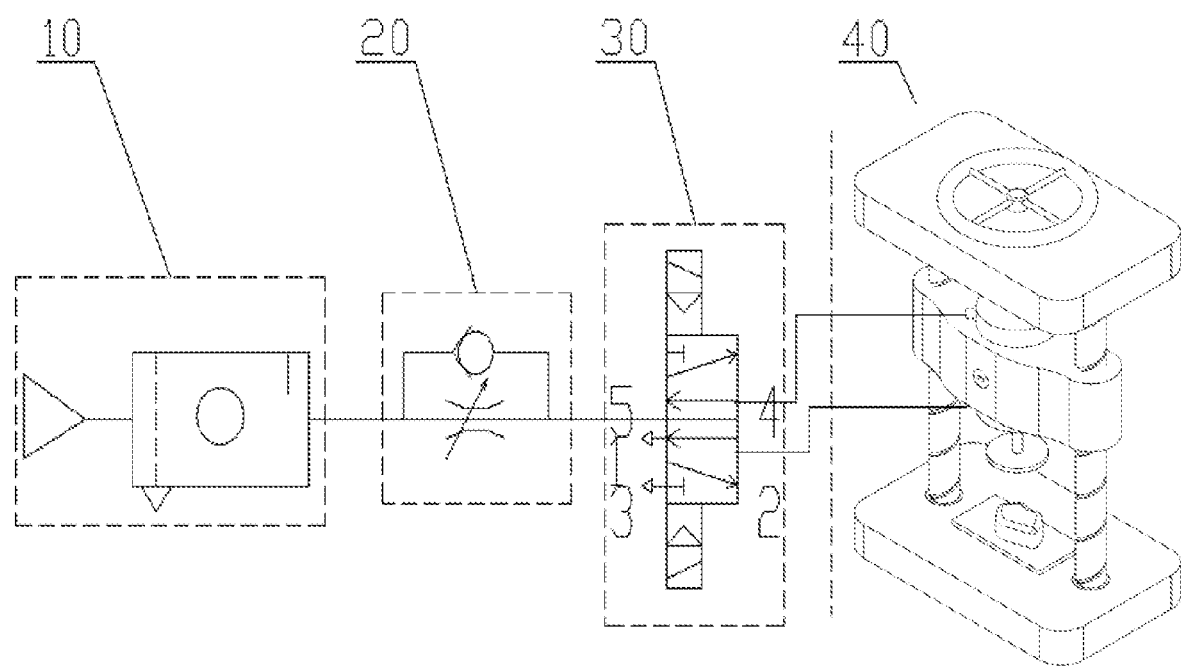
FIG. 1 is a schematic view of a soft tissue simulator for magnetic resonance testing according to the present invention.
Figure 2:
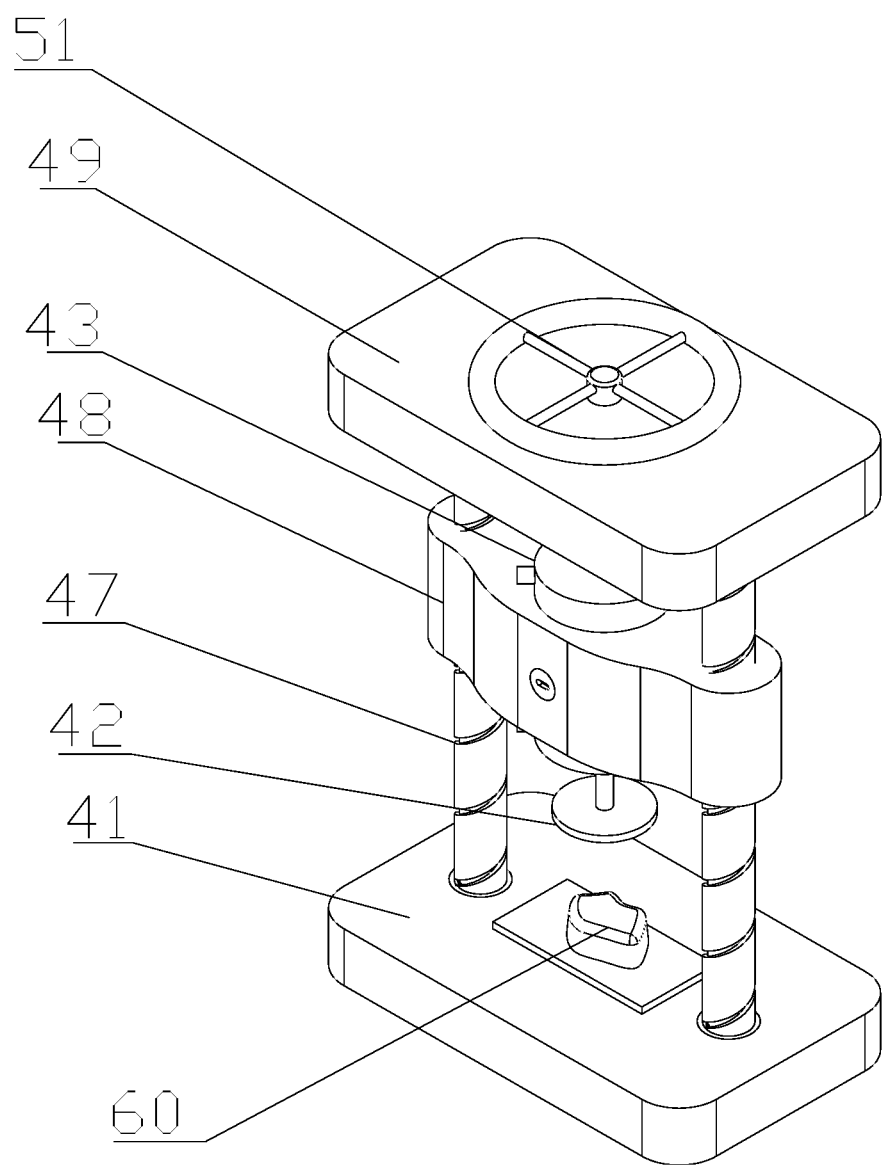
FIG. 2 is a schematic view showing a base for installing an indenter and sample holder according to the present invention.
Figure 3:
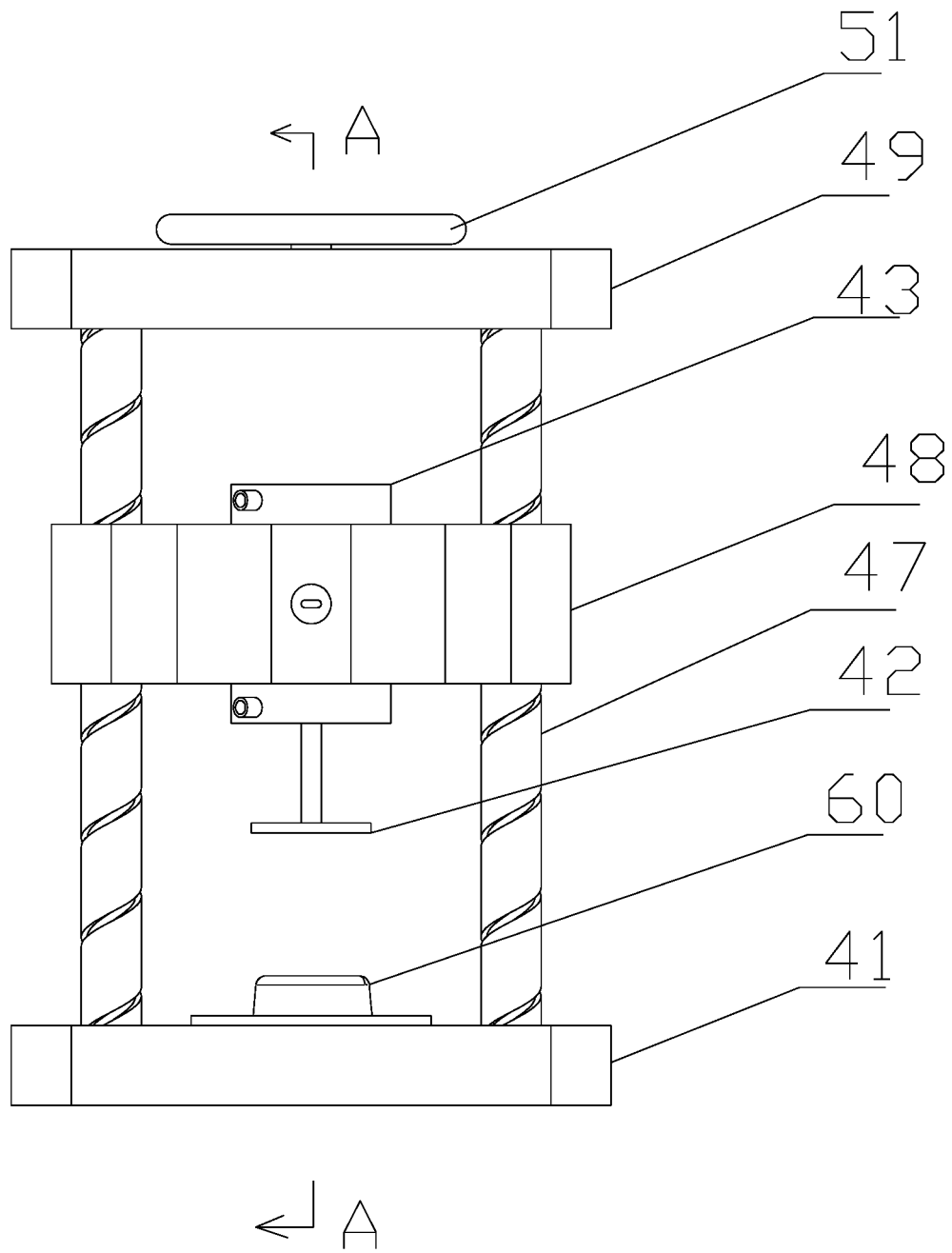
FIG. 3 is a front view of the base.
Figure 4:
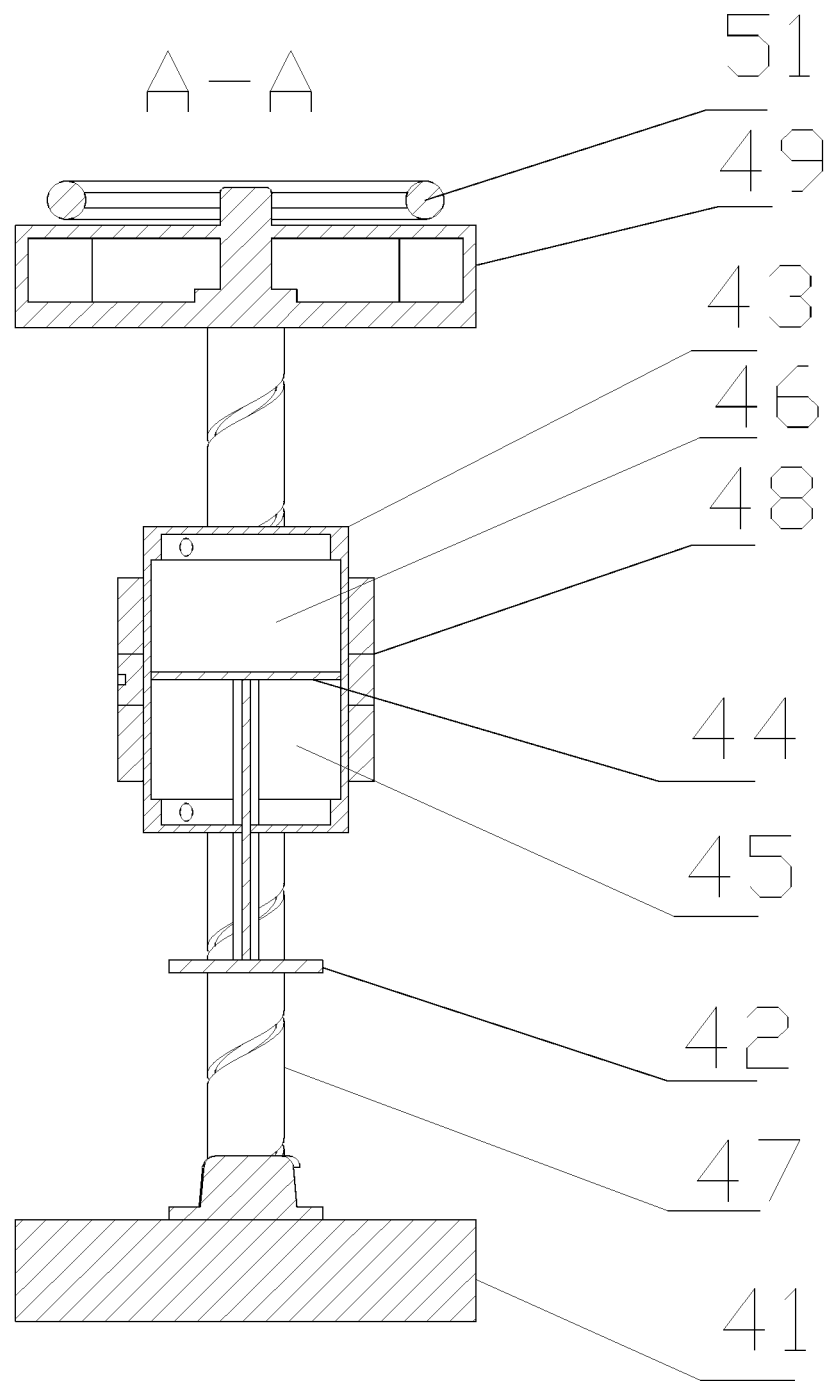
FIG. 4 is a sectional view along a line A-A in FIG. 3.

Referring to FIG. 1 to FIG. 4, a soft tissue simulator for magnetic resonance testing in a preferred embodiment of the present invention includes an air path unit and a sample movement simulation mechanism. The air path unit includes a pneumatic generation source 10, a one-way throttle valve 20, and a two-position five-way solenoid reversing valve 30 that are sequentially connected. The sample movement simulation mechanism 40 includes a base 41 for supporting a soft tissue or organ sample, an indenter 42 facing the sample, and a pneumatic cylinder 43 for driving the indenter 42 to move reciprocally relative to the sample. An adjustment device is disposed on the base 41 for adjusting a distance between the pneumatic cylinder 43 and the sample. The adjustment device includes two screw rods 47 each having one end rotatably connected to the base 41, a sliding platform 48 having two ends threadedly connected to the two screw rods 47 respectively, a top plate 49 rotatably connected to the other end of each of the two screw rods 47, and a handwheel 51 disposed on the top plate 49 for driving the two screw rods 47 to rotate. The pneumatic cylinder 43 is sleeved in the sliding platform 48 and is fastened by bolts.

In the present invention, the indenter 42 is driven in a pneumatic manner to move. The indenter 42 is driven by the pneumatic cylinder 43. Specifically, the pneumatic cylinder 43 of the present invention is separated into a first chamber 45 and a second chamber 46 by a piston 44. The piston 44 is connected to the indenter 42. In the present invention, the first chamber 45 and the second chamber 46 of the pneumatic cylinder 43 are respectively connected to an first air outlet and a second air outlet of the two-position five-way solenoid reversing valve 30, such that the indenter 42 is driven by the piston 44 to move reciprocally. When air enters the first chamber 45 of the pneumatic cylinder 43 through the first air outlet of the two-position five-way solenoid reversing valve 30, under the effect of air pressure, the piston 44 moves downwardly. When air enters the second chamber 46 of the pneumatic cylinder 43 through the second air outlet of the two-position five-way solenoid reversing valve 30, under the effect of air pressure, the piston 44 moves upwardly. The piston 44 moves up and down to drive the indenter 42 to move reciprocally relative to the sample.

The distance between the pneumatic cylinder 43 and the base 41 needs to be adjusted when samples of different sizes are placed on the base 41. During adjustment, the handwheel 51 is rotated to rotate the two screw rods 47, such that the sliding platform 48 moves upwardly or downwardly along the two screw rods 47, to drive the pneumatic cylinder 43 to rise or descend relative to the base 41. In the present invention, the two ends of each of the screw rods 47 are rotatably connected to the base 41 and the top plate 49 by a bearing respectively, such that the two screw rods 47 can rotate relative to the base 41 and the top plate 49. Ends of the two screw rods 47 inside the top plate 49 are in transmission connection with handwheel 51 by racks, and thus the two screw rods 47 can be rotated by rotating the handwheel 51. To enable the air provided by the pneumatic generation source 10 to apply sufficient air pressure to the piston 44, the pneumatic generation source 10 in the present invention is an air compressor that produces compressed air.

A method for simulated testing using the foregoing soft tissue simulator for magnetic resonance testing includes the following steps:

(1) a soft tissue or organ sample 60 having a suitable size is placed on a glass slide, and the glass slide with the sample is placed on the base 41 such that the sample contact the indenter 42, or alternatively, a soft tissue or organ sample is placed on the glass slide, and the glass slide with the sample is placed on the base 41, then, according to the size of the sample, the handwheel 51 is rotated to adjust the height of the sliding platform 48 on the two screw rods 47 such that the indenter 42 contact the sample 60;

(2) the pneumatic generation source 10 is activated, and the direction of the two-position five-way solenoid reversing valve 30 is controlled, such that the first air outlet is in fluid communication with the first chamber 45 or the second air outlet is in fluid communication with the second chamber 46, and the indenter 42 retract or press the sample, then the direction of the two-position five-way solenoid reversing valve 30 is adjusted, and the indenter 42 produces a periodic movement or a unidirectional movement, wherein the one-way throttle valve 20 may be opened at the same time to control a flow amount of compressed air; and (3) the pneumatic generation source 10 is adjusted and controlled based on physical and mechanical characteristics of soft tissue in magnetic resonance, to simulate the movement of a human organ or the movement of soft tissue in human testing.

The working principle of the present invention is as follows:

In an initial position, the right position of the two-position five-way solenoid reversing valve 30 is connected. Compressed air passes through an air inlet 1 of the two-position five-way solenoid reversing valve 30 to reach an outlet 2 and enters the first chamber 45 of the pneumatic cylinder 43. The piston 44 drives the indenter 42 to retract. When the two-position five-way solenoid reversing valve 30 is reversed, compressed air acts on the two-position five-way solenoid reversing valve through the left position of the air inlet 1/an air outlet 4, so that the left position of the two-position five-way solenoid reversing valve 30 is connected. Compressed air enters the second chamber 46 of the pneumatic cylinder 43, such that the piston 44 extend, and the indenter 42 press the sample 60. When the two-position five-way solenoid reversing valve 30 is reversed again, the right position of the two-position five-way solenoid reversing valve is connected. In this way, the movement of the piston 44 is controlled to control the movement of the indenter 42.

According to a testing method of physical and mechanical characteristics of soft tissue based on magnetic resonance, the status of a test sample is simulated. The pneumatic generation source 10 is adjusted and controlled to enable the indenter 42 to produce a periodic movement or a unidirectional movement, such that the movement of a human organ or the movement of soft tissue in human testing is stimulated, and a movement status of the test sample is controlled, to obtain a corresponding experimental result.

The above preferred embodiments are described for illustration only, and are not intended to limit the scope of the invention. It should be understood, for a person skilled in the art, that various improvements or variations can be made therein without departing from the spirit and scope of the invention, and these improvements or variations should be covered within the protecting scope of the invention.

What is claimed is:

1. A soft tissue simulator for magnetic resonance testing, comprising:
   a base for supporting a soft tissue or organ sample;
   an indenter facing the sample;
   a pneumatic cylinder for driving the indenter to move reciprocally relative to the sample, the pneumatic cylinder being separated into a first chamber and a second chamber by a piston which is connected with the indenter; and
   an air source for supplying air to the pneumatic cylinder, the air source comprising a pneumatic generation source and a reversing valve connected to the pneumatic generation source and having a first air outlet and a second air outlet, the first air outlet and the second air outlet of the reversing valve being in fluid communication with the first chamber and the second chamber of the pneumatic cylinder respectively.

2. The soft tissue simulator for magnetic resonance testing as claimed in claim 1, wherein an adjustment device is disposed on the base for adjusting a distance between the pneumatic cylinder and the sample, the adjustment device comprising two screw rods each having one end rotatably connected to the base, a sliding platform with two ends being threadedly connected to the two screw rods respectively, a top plate rotatably connected to the other end of each of the two screw rods, and a handwheel disposed on the top plate for driving the two screw rods to rotate, and the pneumatic cylinder being disposed on the sliding platform.

3. The soft tissue simulator for magnetic resonance testing as claimed in claim 1, wherein a one-way throttle valve is connected between the pneumatic generation source and the reversing valve.

4. The soft tissue simulator for magnetic resonance testing as claimed in claim 3, wherein the reversing valve is a two-position five-way solenoid reversing valve.

5. The soft tissue simulator for magnetic resonance testing as claimed in claim 3, wherein the pneumatic generation source is an air compressor that produces compressed air.

6. A method for simulated testing using the soft tissue simulator for magnetic resonance testing as claimed in claim 1, comprising steps of:
   (1) placing a soft tissue or organ sample having a suitable size on the base, and making the sample contact the indenter;
   (2) activating the pneumatic generation source and controlling the direction of the reversing valve, such that the first air outlet is in fluid communication with the first chamber or the second air outlet is in fluid communication with the second chamber, and the indenter retract or press the sample, and then adjusting the direction of the reversing valve, to enable the indenter to produce a periodic movement or a unidirectional movement; and
   (3) adjusting and controlling the pneumatic generation source based on physical and mechanical characteristics of soft tissue in magnetic resonance, to simulate the movement of a human organ or the movement of soft tissue in human testing.

7. A method for simulated testing using the soft tissue simulator for magnetic resonance testing as claimed in claim 2, comprising steps of:
   (1) placing a soft tissue or organ sample on the base, and rotating the handwheel to adjust a height of the sliding platform on the screw rods according to the size of the sample, such that the indenter contacts the sample;

(2) activating the pneumatic generation source and controlling the direction of the reversing valve, such that the first air outlet is in fluid communication with the first chamber or the second air outlet is in fluid communication with the second chamber, and the indenter retract or press the sample, and then adjusting the direction of the reversing valve, to enable the indenter to produce a periodic movement or a unidirectional movement; and (3) adjusting and controlling the pneumatic generation source based on physical and mechanical characteristics of soft tissue in magnetic resonance, to simulate the movement of a human organ or the movement of soft tissue in human testing.

8. A method for simulated testing using the soft tissue simulator for magnetic resonance testing as claimed in claim 3, comprising steps of:

(1) placing a soft tissue or organ sample having a suitable size on the base and making the sample contact the indenter, or, placing a soft tissue or organ sample on the base, and rotating the handwheel to adjust a height of the sliding platform on the screw rods according to the size of the sample, such that the indenter contacts the sample;

(2) activating the pneumatic generation source, opening the one-way throttle valve and controlling the direction of the reversing valve, such that the first air outlet is in fluid communication with the first chamber or the second air outlet is in fluid communication with the second chamber, and the indenter retract or press the sample, and then adjusting the direction of the reversing valve, to enable the indenter to produce a periodic movement or a unidirectional movement; and (3) adjusting and controlling the pneumatic generation source based on physical and mechanical characteristics of soft tissue in magnetic resonance, to simulate the movement of a human organ or the movement of soft tissue in human testing.

* * * * *